United States Patent [19]

Wang

[11] 4,382,181
[45] May 3, 1983

[54] DETECTION OF ATOMS USING MONOCHROMATIC X-RAYS

[76] Inventor: Chia-Gee Wang, P.O. Box 211, Millwood, N.Y. 10546

[21] Appl. No.: 239,135

[22] Filed: Feb. 27, 1981

Related U.S. Application Data

[63] Continuation-in-part of Ser. No. 116,177, Jan. 28, 1980, abandoned, which is a continuation-in-part of Ser. No. 70,586, Aug. 29, 1979, Pat. No. 4,239,966.

[51] Int. Cl.³ .......................................... G01N 23/20
[52] U.S. Cl. ..................................... 250/305; 378/45
[58] Field of Search ............... 250/458, 459, 277, 275, 250/444, 493.1; 378/120

[56] References Cited

U.S. PATENT DOCUMENTS

| | | | |
|---|---|---|---|
| 3,919,548 | 11/1975 | Porter | 250/277 |
| 4,085,331 | 4/1978 | Thackray | 250/493.1 |
| 4,239,966 | 12/1980 | Wang | 250/275 |

*Primary Examiner*—Davis L. Willis
*Assistant Examiner*—T. N. Grigsby
*Attorney, Agent, or Firm*—Hayes, Davis & Soloway

[57] ABSTRACT

A method and apparatus for detecting, in a specimen, atoms, of an element having an atomic number of at least 20, comprising irradiating the specimen with monochromatic X-rays having a wavelength capable of inducing an inner shell ionization of the atoms with subsequent auger cascade and recording the emission of the auger electrons emitted by the cascade.

41 Claims, 6 Drawing Figures

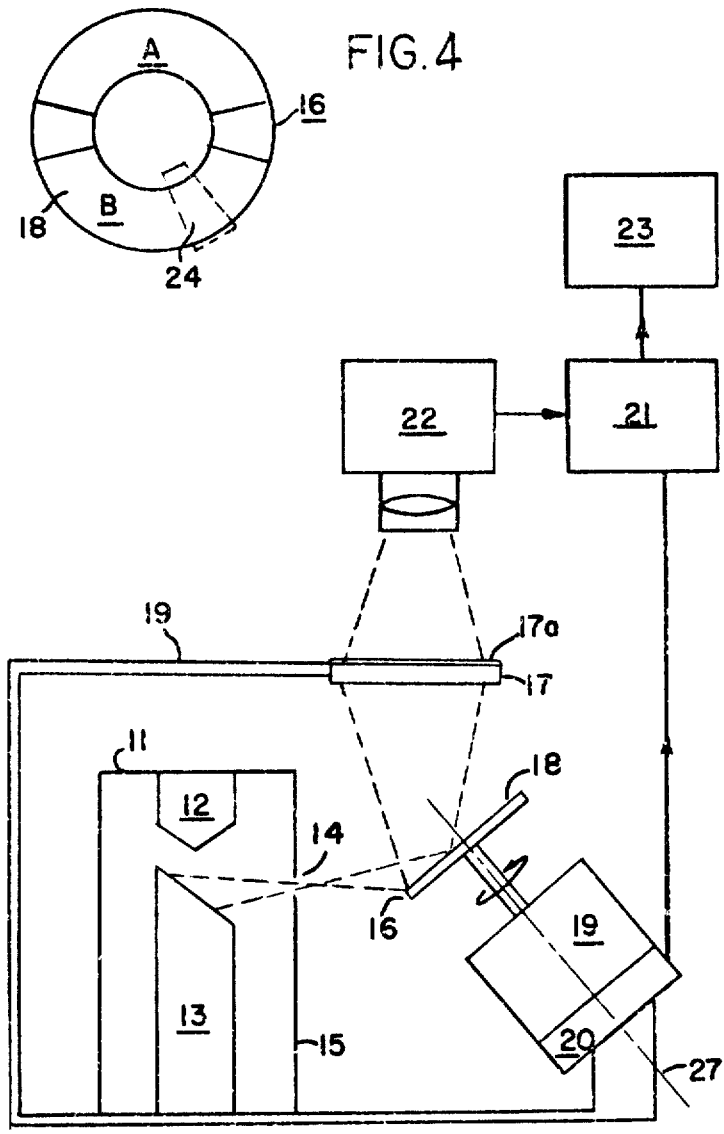

DETECTION OF ATOMS USING MONOCHROMATIC X-RAYS

This is a continuation-in-part of applicant's U.S. Ser. No. 116,177 filed Jan. 28, 1980 and now abandoned which was itself a continuation-in-part of applicant's U.S. Ser. No. 070586 filed Aug. 29, 1979 and now Pat. No. 4,239,960.

This invention relates to the detection of atoms of a desired element in a specimen and particularly, although not exclusively, to the detection of iodine atoms or bromine atoms in a biological specimen.

It is known that the irradiation of elements having an atomic number of 20 or more by monochromatic X-rays on the K-edge of the atoms of the element will produce an inner shell ionization a fraction of which leads to an auger cascade ejecting electrons from the atom recordable on a photographic emulsion. In the case of iodine (I) as many as 18 auger electrons may be created from an inner shell ionization while in the case of bromine (Br) as many as 13 auger electrons may be created. In the present invention it is proposed to utilize this phenomena to detect the quantity and distribution of atoms of an element present in a specimen, for example a biological specimen.

DNA genomes in the cell structure of a biological specimen are not usually visible under a light microscope, scope, but become visible when stained with certain basic dyes. When the genome is metabolically active, it extends over a relatively larger region, can only be stained lightly and shows considerable variation of shade. When inactive, the DNA strands which are tightly twisted and folded together can be stained deeply and show sharply demarcated lumps or granules. Much genetic information has been learned from the morphology of chromatids which can be clearly examined during the metaphase of mitosis where the mitotic process was stopped with colchicine and the cells squashed and stained. Similarly, the use of certain fluorescent dyes to intercalate between pairs of DNA bases, and use the lumination of the dye under ultraviolet light or X-ray, provides a clear outline of the chromosome. In order to learn the metabolic functions on a molecular level, labelled molecules, such as the $^3$H-thymidine is often used in autoradiography. Electrons, emitting from the tritium decay, can be recorded in a photographic emulsion. But the dosage of the radioactivity is such that it must not interfere with the metabolic processes, and the radioactive decay time of tritium at a half-life of 12 years is often too inconveniently long. A more recent tool is the use of restrictive enzymes to cut the genome at some designated sections. The use of these methods, and of some combinations of them, have provided genetic research with powerful tools.

According to the present invention there is provided a method of detecting, in a specimen, atoms, of an element having an atomic number of at least 20, comprising irradiating the specimen with monochromatic X-rays having a wavelength to induce an inner shell ionization of said atoms with subsequent auger cascade, and detecting the auger electrons emitted by the cascade.

According to the invention there is also provided an apparatus for detecting, in a specimen, atoms of an element having an atomic number of at least 20, comprising a source of monochromatic X-rays having a wavelength to induce an inner shell ionization of said atoms with subsequent auger cascade, and means for detecting the auger electrons emitted by the cascade.

In both the method and apparatus forms of the present invention the detection means is, in one form of the invention, a photographic emulsion which includes substantially no atoms of the element the detection of which is desired.

In a preferred form of the invention the source of monochromatic X-rays of the desired wavelength is a secondary radiator including atoms which are excited by X-rays from an X-ray generator to produce secondary radiation in the form of X-rays of the desired wavelength The secondary source of radiation can also be a Bragg Diffractor.

The method and apparatus of the present invention is particularly useful for ascertaining the quantity and distribution of atoms of an element which have been added to a biological sample as a "label". In a particular application the atoms of the element to be detected are used to "label" a DNA molecule or certain proteins with an element being non-radioactive (cold) under metabolic conditions, for example, bromine or iodine. As the elements concerned are virtually non-toxic, relatively large amounts can be administered for irradiation by a monochromatic X-ray on the K-edge of the element to be detected to produce inner shell ionization. Upon the occurance of the ionization, electrons in the outer shells fall in, with certain probability, to fill the inner hole. The difference of potential energy between different shells that the in falling electron switches, may or may not lead to a radiative transfer. An auger cascade is a sequence of non-radiative transfer from a single inner hole in which an outer shell electron falls in to fill the hole and due to its difference in potential energy ejects a neighbouring electron, creating two holes in the process. Following this more outer shell electrons fall in to fill the holes and their difference in potential energy results in the ejection of still more electrons from the atom. As many as 18 auger electrons may be created from an iodine inner shell ionization and as many as 13 from bromine.

The auger electrons are mostly of low energy and deposit more their kinetic energy within a very short distance in a biological environment thereby creating extremely concentrated localized multiple ionizations. In contrast, the X-ray which initiates the inner hole is almost transparent to the medium. In the presence of a photographic emulsion, it will record the auger cascade but not the X-ray photons. Due to the fact that auger cascade begins from an inner hole, it is independent of the chemical state of the atomic binding. In the case of bromine, for example, it makes no difference whether the element is contained in BrdU or in AgBr. To detect Br in a specimen, the photographic emulsion must not contain the element Br, similarly, if iodine is the target element, it must not be present in the emulsion. Otherwise, one cannot distinquish whether if the auger electrons originate from the specimen or from the emulsion itself.

A method and appratus in accordance with the present invention will now be described, by way of example, with reference to accompanying drawings in which:

FIG. 3 is a diagrammatic representation of an alternative embodiment to that of FIG. 2;

FIG. 4 shows the reflective face of a secondary radiator for use in the apparatus of FIG. 2 or 3;

Figure 1:
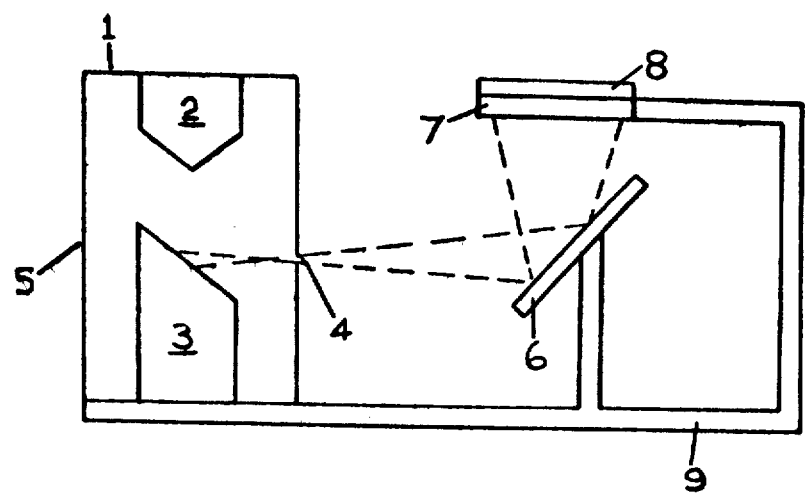
FIG. 1 is a diagrammatic representation of a basic form of apparatus.

With reference to FIG. 1 of the drawings a conventional X-ray tube 1 has a cathode 2 and a target electrode or anode 3 surrounded, except for an X-ray emission window 4, by a shield 5. A secondary radiator 6 is disposed to receive X-rays emitted by the X-ray tube 1 through the window 4 and to emit secondary radiation, induced by these X-rays, in a direction toward a specimen 7 which is coated on the side of the specimen remote from the secondary radiator 6 by a photographic emulsion 8. The X-ray tube, secondary radiator and coated specimen are supported relative to one another by a support structure 9.

The secondary radiator 6 includes a substantial number of atoms of an element capable of emitting fluorescent X-ray photons at desired energies. The secondary radiator 6 may be entirely constructed from said element, which element has an atomic number of at 20. When the secondary radiator 6 is exposed to the X-rays emitted through the window 4, the incident radiator is absorbed leading to excitation of the elements characteristic lines as if it were the source, but with a reduced photon density and without the bremsstrahlung. This secondary emission is a monochramatic X-ray having a wavelength corresponding to the elements characteristic lines and is emitted by the secondary radiator 6 toward the specimen 7. These monochramatic X-rays, which are on the K-edge of the element, created an inner shell ionization of the atoms of the element to be detected in the specimen thereby initiating an auger cascade with the consequent emission of auger electrons which are mostly of low energy and deposit most of their kinetic energy within a very short distance in the environment of the specimen, for example a biological specimen, thereby creating extremely concentrated localized multiple ionizations. In contrast, the specimen, other than the element concerned, and the photographic emulsion are almost transparent to the monochromatic X-rays with the result that the photographic emulsion will record the auger cascade but not the X-ray photons.

Although the preferred manner of producing monochromatic X-rays of the desired wavelength in the present invention is by the use of the secondary radiator, this is but one of three possible methods which could be used and which are intended to fall within the boundaries of the present invention. A second method is the use of an appropriate anode material and voltage plus some filtering, and a third method is the use of a Bragg diffractor.

In a conventional X-ray machine, the potential drop between the anode and the cathode derives directly from the DC rectification of the output of an AC transformer. The sinusoidal line power is first transformed into high voltage, retaining the AC line frequency, and the simple rectification changes nothing but the negative half-cycles into the positive cycles. As a result, the voltage supplying the X-ray tube changes continuously from zero to $V_{peak}$. For a monochromatic X-ray output where only an optimum of potential is needed. Most levels do not produce the desired X-ray photons and is therefore wasted. In order to have a steady monochramatic X-ray output, it is necessary to have a DC power supply with proper current and voltage characteristics.

The second important consideration for the design of a X-ray tube is target material of the anode. For a typical metal target, it produces a K-edge specific to the metal element and a bremsstrahlung tail. If the desired monochromatic X-ray happens to lie within the width of the K-edge peak, a proper choice of $V_{peak}$ gives a high energy cutoff and the window material of the tube filters away photons of longer wavelength, including the bremsstrahlung tail. under continuous electron bombardment, the target must dissipate almost all the electron energy (99.8%) in the form of heat. Usually heat dissipates in the form of black-body radiation at high temperature, or is carried away by circulating oil or water. Because of the heat dissipation, most of the target material are metals.

This second method of producing monochromatic X-rays involves the use of fluorescent materials that can produce X-ray emmisions at desired energy levels.

The third method of producing a monochromatic X-ray is the use of a crystal diffractor. The Bragg diffraction gives a condition:

$$2\, d\sin \theta = n\lambda$$

that from a point source to a point target T, at a given diffraction angle $\theta$ and the crystal spacing d, only photons, with wavelength $\lambda$ satisfying the Bragg condition can be coherently reflected. Most of the photons diffracted are at the first harmonic $n=1$. The diffractor is usually curved in order to focus the monochromatic photons onto the target material. There are now commercially available diffractors with the proper spacing to cover each element of the K-edge radiator for any element with $Z \geq 10$. However, a suitable diffractor is expensive and photon number density of the output is low.

Accordingly the secondary radiator method of producing monochromatic X-rays of the desired wavelength is the preferred method for use in basic form of the present invention.

The use of X-ray photons in accordance with the present invention to do chemical analysis is to some extent comparable with histochemical analysis. In histological studies, very soft X-rays are used to examine the transmission characteristics of a very thin tissue. In order to obtain the maximum contrast, the preparation of the specimen (thickness, levels of various mineralizations, etc.), the X-ray voltage, choice of the target and the window materials must all be critically compared. In order to avoid the absorption of the soft X-ray photons by air, various vacuum-mount cameras are required for the study. In some contact studies of cytological detail, a resolution as high as 0.2 $\mu$m can be obtained. In the present invention, hard X-ray photons are employed. As these are very penetrating to the specimen as well as the emulsion, and the photographic record is initiated from auger electrons, which give extremely efficient linear-energy-transfer to sensitize the emulsion. With this high contrast the design considerations result in equipment which is relatively simple.

Although not limited to use in the analysis of biological specimens, the present invention is useful in studies of DNA and protein structures in biological specimens with bromine being suitable as a "label" for DNA molecules and iodine being suitable as a "label" for protein.

As will be apparent from the above description the choice of photosensitive material forming the photographic emulsion is important. In the following description the use of a target element of iodine or bromine is considered. However, the concepts involved will be seen clearly to apply in situations where the specimen may not be a biological specimen and where the target element is not iodine or bromine.

Photographic images are formed through the deposit of silver. Most negative emulsions are composed mainly of AgBr crystals (grains) suspended in a gelatin and coated with a thin layer of supercoating to prevent sensitization by pressure (handling protection). The supercoating is too thick a layer for low energy electrons to penetrate. Liquid emulsions, such as Kodak NTB2, NTB3 etc., are therefore used to coat directly on the specimen slide for the exposure of $^3$H-thymidine in autoradiography. Emulsions for positive paper composed mainly of AgCl crystals without the supercoating. AgCl crystals are much slower than AgBr crystals. For typical X-ray film, its response to X-ray irradiation is only 2–7% relative to photons of visible range, and screen-type intensifiers are therefore often used to transform (fluorescence) photons from X-ray to that of visible in order to increase the film's sensitivity. Normal X-ray films also have double coatings, one for fast exposure and another for slow, in order to increase the exposure depth.

The formation of a metallic silver grain requires several steps. A latent image, initated with as little as only a few silver atoms at a sensitivity speck of the grain, can be caused by photoelectrons or by ionizing charged particles passing nearby. The neutralized silver atoms at the sensitivity speck are stabilized and act as a catalyst to form a development centre attracting additional metallic silver during the process of development. Depending upon vigor of the development and the accessability of the sensitivity specks to the developer, a latent image speck may or may not be of sufficient size to form a development centre. For transillumination, images block out the illuminating light and dark images are formed whenever there are large deposit of silver grains. For dark-field illumination, light shines at the images from an oblique angle each silver grain becomes a source of relected light and becomes instead the bright area of the image film. The dark-field illumination can reduce the light exposure, retaining the same image resolution. With relatively limited exposure, we shall make use of the dark-field illumination.

The monochromatic X-rays for triggering an auger cascade in bromine have a photon energy of 13.47 KEV and for iodine have a photon energy of 33.17 KEV.

A filter may be used to eliminate wavelengths of X-rays, from the X-ray generator, below the energy of the wavelength of the target element. In this arrangement the specimen and the emulsion and/or the secondary radiator need not be free elements in which an auger cascade is induced by X-rays of a wavelength filtered out by the filter.

In order to record Bromine atoms in the specimen, Gold (Au) may be used as the material for the secondary radiator and the specimen coated with AgCl or AgI as the emulsion material to detect the auger electrons from bromine. Similarly, for iodine atoms, Barium peroxide (BaO$_2$) can be the secondary radiator and AgBr the emulsion material. For greatly under-exposed images with silver atoms, dark-field illumination can be used with the help of an electronic-image intensifier with the image composed on a television picture tube. Note that with the usual transillumination, when there are too many silver grains, or simply an over-exposure, the image information or resolution is reduced as one cannot distinguish one grain point from another. In dark-field illumination, on the other hand, under-exposure involves smaller number of grains, but the resolution of the image is not necessarily reduced. With the help of a television lens, the image is recomposed, and in effect, each grain size is amplified to retain the same image quality. With this method, many emulsions of slow exposure speed, such as emulsions composed of AgCl crystals, can become useful. This under-exposure without the loss of resolution is of great importance in many fields of application, for example, medical examinations with X-rays, (e.g. mammography, dental pictures) and in astronomy where the reduction of exposure time can be equated to an increase in telescope size.

While the present invention has been described with particular reference to the detection and recordal of atoms of an element used to "label" a biological specimen, it will be appreciated that the method and apparatus of the present invention is applicable to the detection and recordal of the presence of particular elements and the distribution of their atoms in a wide variety of specimens in a wide variety of sciences and technologies (e.g. metallurgy, geology, environmental engineering, polution detection, production and quality control).

It will further be appreciated that while the basic form of the present invention has been described with respect to a particular method and a particular apparatus, many variations will be apparent to a man skilled in the art and that the variations fall within the scope of the present invention as claimed hereinafter.

For example:

A. The specimen may be self supporting or supported on a carrier, for example a glass slide, the material of which will not respond to the monochromatic X-rays to produce any discernible image on the photographic emulsion. These materials will, of course, be readily apparent to those skilled in the art and easily determined by simple experiment.

B. The photographic emulsion may be coated on the specimen itself or on the carrier, between the secondary radiator and the specimen or on the side of the specimen remote from the secondary radiator, between the specimen and the carrier or on the side of the carrier remote from the specimen etc. The critical criteria being that the photographic emulsion be sufficiently adjacent the specimen for the recordal of the localized ionizations produced by the auger electrons of the atoms of the element in the specimen which is to be detected.

C. The means for detecting the localized multiple ionizations produced by the auger electrons is not restricted to the use of photographic emulsion and may involve, for example, a vidicon tube or matrix semiconductor type image intensifier, a charge coupled device (CDC), scintilation counter, and means for displaying or recording these.

More advanced forms of the present invention (FIGS. 2, 3 and 4) involve the use of tunable beams of relatively monochromatic X-ray photons to probe the specimen and the use of induced X-ray fluorescent photons of the designated heavy element, such as the K-lines of the iodine, as an indication of the presence of such element in the specimen.

Each chemical element, depending on the electric charge of its nucleus, has well defined energies of its inner shell electrons, and these energy levels are independent of the chemical state of the atom. Irradiating with X-ray photons having an energy at just above the absorption edge of an inner shell, the absorption crosssection of the inner shell, the absorption crosssection of the photon by the designated element is very large. As soon as the photon energy drops to a level slightly below the absorption edge, the crosssection is greatly reduced. Non-resonant events such as photoelectrons and other fluorescent photons that are not sensitive to change of the photon energy remain essentially the same. A comparison of scattering signals with photons at energies above and below the absorption edge, or in other words, from the difference of the two signals, one gets a purely resonant signal without the non-resonant noises. The resonant signal relates to only the inner shell ionization of the designated element, and therefore the amount of the designated element in the specimen. The present invention uses X-ray tube plus a secondary radiator as a source for the tunable monochromatic X-ray source.

Figure 2:
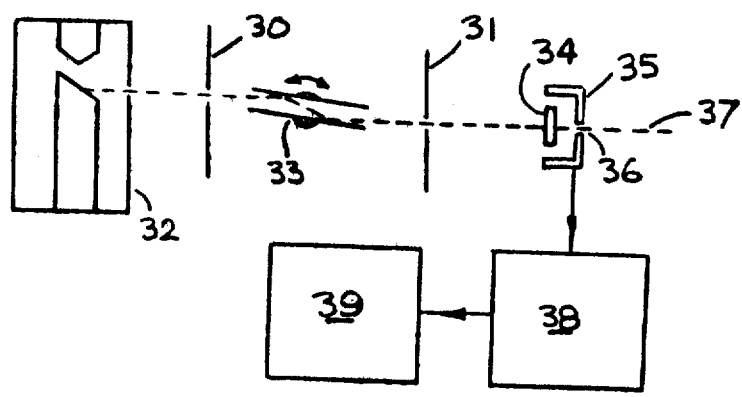
FIG. 2 is a diagrammatic representation of a more advanced apparatus.

The secondary radiator can be a parallel Bragg diffractor (spectrometer) where the diffracted photon energy depends very sensitively on the angle of diffraction of the spectrometer. FIG. 2 diagrammatically illustrates such an arrangement, using collinators 30, 31 between the X-ray source 32 and the Bragg diffractor 33 and between the Bragg diffractor 33 and the specimen 34. The flourescent photons emitted by the designated element in the specimen are detected by a scintillation detector 35 having a centrally disposed opening (36) for passage of the X ray beam 37. By switching the angle of diffraction of the diffractor 33 with certain regularity (constant switching frequency), the photon energies can be controlled at just above or below the absorption edge of the designated element. A lock-in amplifier 38, (e.g. Ithaco Inc's "Dynatrac" 393 lock-in) receiving signals from the photodetector as well as switching information (the chopping frequency), easily sorts out the noise and the signal for recordal by a counter 39.

In an alternative construction, the secondary radiator is constructed by a spinning disc composed of two different elements, with each element occupying part of the disc (FIG. 4). With reference to FIG. 4, element A would emit fluorescent photons at energies just above the absorption edge of the designated element while element B would emit photons at energies just below. The spinning rate of the disc serves as to provide the chopping or switching frequency for the lock-in amplifier. The elements can be electroplated on a copper base, for example.

Although the signals thus obtained from a lock-in amplifier do not provide the position of the designated element in the specimen, they can provide quantitative information in a rather quick and simple manner. In a case where the positional information is desired as well, one can use a Charged-Coupled-Device as the detector.

An alternative apparatus for use in performing its advanced method using a spinning secondary radiator will now be described with reference to FIGS. 3 and 4. With reference to FIG. 3 a conventional X-ray tube 11 has a cathode 12 and a target electrode or anode 13 surrounded, expect for an X-ray emission window 14, by a shield 15. A secondary radiator 16 is disposed to receive X-rays emitted by the X-ray tube 11 through the window 14 and to emit secondary radiation, induced by these X-rays, in a direction toward a specimen 17. The X-ray tube, secondary radiator and coated specimen are supported relative to one another by a support structure 19.

The secondary radiator 16 is rotated about an axis 27 normal to its radiating surface 18 by a motor 19 at 3000 rpm. This rotation may be continuous or intermittent. A rotation detector 20 is connected to the motor 19 to detect and provide a signal representing the rate of spin or intermittent rotation and phase of rotation of the secondary radiator 18 and this signal is fed as one input of lock-in amplifier 21 (eg Ithaco's "Dynatrac" 393 Lock-in). The X-ray emission from the inner shell ionization of atoms in the specimen is converted to visible light by the tellurium doped matrix of lucite 17a disposed closely adjacent and overlaying the specimen 17. This visible light emission is detected by a video camera 22 (with an image intensifier in some arrangements) the video signal output from which is fed to a second input to the lock-in amplifier 21 which provides an output, representing the difference between the fluorescent ionization of atoms of the specimen 17 generated by secondary radiator from element A and element B of the secondary radiator 16, for supply to a display or recording device 23. The X-ray emission from source 11 is of a beam cross-section whereby the area of the disc 16 exposed thereto is only the area 24. Hence element A and element B are never exposed to the X-rays at the same time. Direct X-rays from radiator 18 are blocked by a metal matrix 17b and cannot reach the lucite matrix 17a. Both metal matrix 17b and lucite matrix 17a have the same matrix from and are optically aligned. Only the part of specimen not covered by the metal area of matrix 17b can receive the X-rays while the part of specimen in the shadow of the matrix is shielded from the X-rays. The doped lucite matrix 17a therefore receives X-ray from only the specimen and not from the radiator 18. The specimen and matrix can relatively moved to expose different portions of the specimen to the X-rays from the radiator 18.

Using a spinning secondary radiator, a simple change of angle of a Bragg defractor or a change of the fluorescent material of the secondary radiator to provide selected photon energies, a signal from a designated element incorporated into the biological specimen and noise from all other elements in the specimen is produced. A slight change of the photon energy changes the signal but not the noise. In a resonanting mode, the detector senses the signal as well as the noise, while in a nonresonanting mode, the detector senses only the noise. The secondary radiator 16 receiving X-rays from the source 11 on a discrete area, so that only element A or only element B receive the X-rays, switches the photon energies between the two modes at certain frequency, and a lock-in amplifier, synchronized with this switching frequency, easily sorts out the pure signal from the noise, and thereby greatly enchances the sensitivity of the signal. The designed element, be it Bromine (Br) or (I) Iodine incorporated in the specimen, can be quantitively read out as the signal level and recorded.

In order to concentrate photons mainly at energies slightly above 13.47 KeV to shine at the specimen and create the desired inner shell ionization of Br, we can use Gold (Au), as a target on the secondary reflector, which has a $L_{II}$ absorption edge, at 13.7361 KeV. From this one gets $L_{II}O_{IV}$ line at 13.7304 KeV, $L_{II}O_{I}$ at 13.6260, $L_{II}O_{III}$ at 13.679, $L_{II}O_{II}$ at 13.662, and $L_{II}N_{VI}$ at 13.6487. A Bismuth target area on the secondary reflector with its $L_{III}$ absorption edge at 13.426 KeV can be used in filtering away most of the nonresonant noise photons below the Br absorption edge.

Iodine is clearly a preferred designated element in X-ray immunossay. With the iodine's K-edge level at 33.1665 KeV, the monochromatic photon energies from a Bragg spectrometer can be 33.17 and 33.16 KeV. Other elements such as mercury or lead in a tissue can be assessed in the same manner, except that with a higher energy level of their k-edges, the target voltage of the X-ray tube must be considerably raised.

It will be appreciated that the advanced forms of the present invention provide an economical means of obtaining a quantitative measure of an element in a specimen. Distributive information can be obtained by comparative study of spacial distributing with and without resonant photons. Data processing equipment may be programmed to reform this study.

It will also be appreciated that variations on the use of photographic emulsions for the recordal of the auger activity are possible and, in some circumstances, may be preferable. Such alternative variations include the use of means capable of holding an electrostatic charge indicating the adjacent emission of auger electrons. For example, a mylar film may be placed next to the specimen for the collection of auger electrons, such as those induced by the exposure of bromine to X-ray protons at an energy of 13.5 KeV, with the resulting electrostatic image of the auger electrons indicating the point of emission of those electrons from the bromine atoms. The electrostatic image so produced may be developed by the application of a liquid toner, consisting of carbon or graphite particles in solution, the carbon or graphite particles in the liquid migrating to the charged portions of the image and there being fixed by means well known in the art of xerography to produce a visible image indicating the special distribution and density of bromine atoms in the specimen. The electrostatic image formed could, of course, also be developed by the use of a dry graphite toner or other means well known to xerography.

As will be readily appreciated the vidicon tube detection may be replaced by a charge coupled device (CCD) and that such replacement may simplify provision of information on the spacial distribution.

The array of a charge couple device (CCD) can recall the electrostatis image created by the electrons provided that X-rays which induced the auger emission have an energy greater than 10 KeV. This lower energy limit is necessary as softer X-rays would themselves initiate enough photoelectrons in the CCD to greatly reduce the signal to a noise ratio. Two advantages of using a CCD are the linear signal strength relative to the charge created, coupled with the very large range of that linearity, and the possibility of storing signals from the CCD when it is alternately exposed to the auger emissions resulting from exposure of the specimen to X-ray irradiation at different energy levels, for example, at energies just above and just below a particular absorption edge, with the differences between the signals recorded in each pixel (spot) being subsequently determined and used as a signal to provide a differential output representing the atoms the detection of which is desired with a substantial reduction in background noise. Such an arrangement permits an analysis which is element specific and very sensitive.

Figure 5:
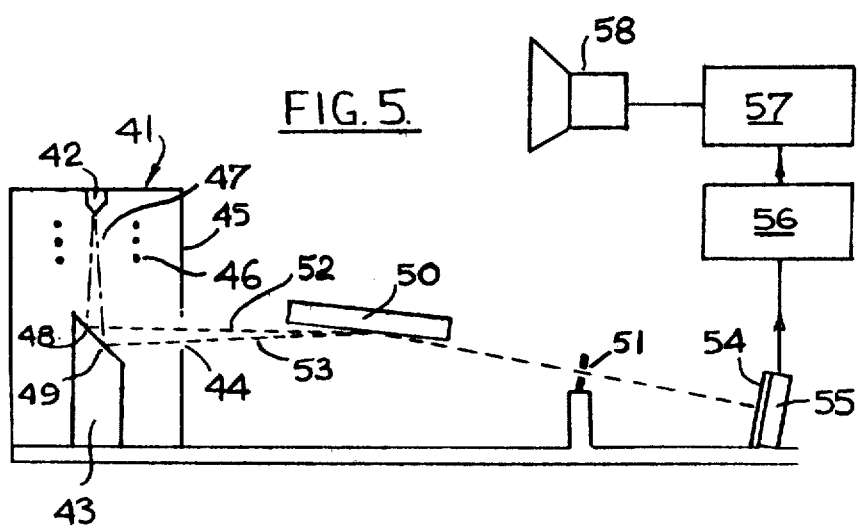
FIG. 5 is a diagrammatic representation of a further embodiment of the apparatus.

The provision of an X-ray beam alternately switching between two desired energy levels may conveniently be provided by the combination of an X-ray generator, a Bragg defractor and an aperture through which the output from the Bragg defractor passes to the specimen and CCD with the components specified being supported in fixed spaced relationship with one another. In this arrangement an X-ray source having a switched or moveable electron beam capable of being switched or moved, to focus onto two different portions of the target is utilized, in order to provide two incident angles of emitted X-rays on the Bragg defractor with the consequent alternative X-ray energy level being provided through the aperture. The switching of the electron beam in the X-ray generator may be achieved using two spaced cathodes, with the power supply being switched alternately between these or by beam deflection means, for example, static, electromagnetic, inductive or capacitive deflection means. Such an arrangement is illustrated in FIG. 5 in which an X-ray tube 41 had a cathode 42 and a target electrode or anode 43 surrounded, except for an X-ray emission window 44, by a shield 45. A deflection yoke 46 is disposed between the cathode and anode and is arranged to be energized to deflect the electron beam 47 so as alternately to fall on two different areas of the target 48 and 49. Disposed in fixed spaced relationship with the X-ray generator 41 is a Bragg defractor 50 and an X-ray aperture 51 to pass X-rays of a desired energy after defraction of the X-ray beam emitted by the X-ray generator 41. As a result of the deflection of the electron beam 47 by the deflection coil 46 the X-ray beam emitted by the X-ray generator will be switched between two different angles of emission to provide, alternately, X-ray beams 52 and 53 which have different incident angles with the Bragg defractor 50 with the consequent change in the angle of specific energy levels of X-ray defracted by the defractor. This will result in alternate energy levels passing through aperture 51 to the specimen 54 in dependence upon the switching of the electron beam in the X-ray generator. A charge couple device (CCD) 55 is placed closely adjacent the specimen to record the activity produced in the specimen by the defracted X-rays passing through the aperture 51. The images produced at the two energy levels resulting from the switching of the electron beam are recorded separately in memory 56 and are subsequently analyzed by a differential amplifier 57 with the difference in the recorded signals being fed to a video tube 58 to provide a visual output representing the spacial distribution of an element or elements the auger output of which is effected by the alternate X-ray energy levels received by the specimen, and/or to other display or recording means (not shown). By this means a sensitive element specific analysis of a specimen is made available in a manner substantially unhampered by obscuring background noise.

In yet another variation of the invention useful X-ray photons are produced by the use of the line spectrum of certain radioactive elements. Nuclei which decay with photon emission, generally emit a great variety of photon energies mostly in the MeV X-ray range. On the other hand, since the radioactive elements are often heavy, they are not transparent, if confined to a solid form, to the softer X-ray photons. These two considerations make most radioactive materials a poor candidate as X-ray sources, particularly those of a point X-ray source. There are, however, a few relatively long lived nuclei which emit a clean (one or only a few lines)

spectrum in the X-ray range. In this variation one of these is coated into a substrate as an area source so as to irradiate a thin biological specimen thereby to induce the Auger electrons preferentially from a desired element in the specimen, and to use the Auger electrons to produce an electrostatic image which can be developed by xerographic means.

The thin specimen, for example, cells or tissues, can be mounted directly on the collector (e.g. a thin sheet of mylar film), and after development can be examined under the optical microscope to view both the electrostatic image as well as the specimen. This can be used, for example, to ascertain whether an element (e.g. Bromine) is incorporated into the cell nucleus, and this method can do the job very quickly, with or without the traditional staining for cell nucleus.

Elements of biological interest whose K-edge energies can be used as a handle, are as follows:
Zn=9.6607 kV; Br=13.470 kV; Ag=25.51 kV; I=33.16 kV; OS=73.856 kV; Au=80.72 kV; Hg=83.109 kV; and Pb=88.005 kV, etc.

A list of relatively long lived X-ray emitters with clean spectra, is as follows:

| Element | Half-Life | Photon Energies (keV) | Decay Products (Half-Life; Energies in keV) |
|---|---|---|---|
| $125_I$ | 60 days | 35.48 | $125m_{Te}$ (58 days; 35.34 and 109.6) and then to $125_{Te}$m stable |
| $129_I$ | $1.7 \times 10^7$ years | 39.58 | $129m_{Xe}$ (8 days; 39.58 and 196.56) and then to $129_{Xe}$, stable |
| $57_{Co}$ | 270 days | 14.4 (8.4%) 122 and higher | $57_{Fe}$, stable |
| $109_{Cd}$ | 450 days | 88.04 | $109_{Ag}$, stable |
| $73_{As}$ | 80.3 days | 13.3 (.44%) 53.4 (~100%) | $73_{Ge}$, stable |
| $44_{Ti}$ | 48 years | 67.85 (10%) 78.4 (14%) | 44 Sc (2.44 days; 271) and then $44_{Ca}$, stable |
| $119m_{Sn}$ | 250 days | 23.83 (~20%) 65 (~100%) | $119_{Sn}$, stable |
| $121m_{Sn}$ | 76 years | 37.15 | $121_{Sb}$, stable |

From the list, $125_I$, $129_I$ and $121m_{Sn}$ can be used for irradiating the Iodine k-edge at 33 keV, and $57_{Co}$ can be used for the Bromine k-edge at 13.47 keV. By avoiding the use of X-ray tube and the monochrometer, this method proves to be very convenient.

Figure 6:
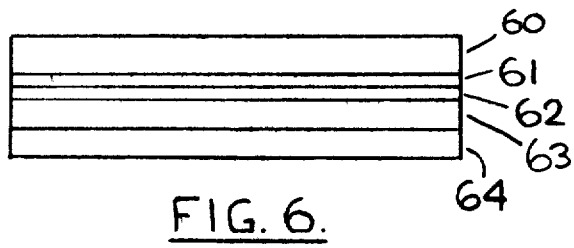
FIG. 6 is a diagrammatic sectional elevation of yet another embodiment of the invention.

With reference to FIG. 6, a substrate 60 coated with a coating 61 of $57_{Co}$ is placed closely adjacent a biological specimen 62 containing atoms of Bromine (Br) the detection of which is desired. Auger electrons emitted by the Bromine in response to irradiation by the X-rays are collected by mylar film 63 placed adjacent the specimen and backed by a positively charged layer 64 behind the collector to hold the electrostatic image in place pending development to fix the image by means of a toner (i.e. a liquid toner, consisting of carbon or graphite particles in solution) using the well-known techniques of xerography.

Although this variation has been described with reference to detection of the auger emissions by means of xerography, it will be appreciated that detection, display and recordal by other arrangements referred to herein also is appropriate including, for example, the use of a charge coupled device (CCD).

Some examples of application for the method and apparatus of the present invention will now be given. It will be appreciated that these examples do not represent an exhaustive discussion of the range of applications.

EXAMPLE I

Direct Identification of Inorganic Elements in Tissue

A direct application of the method of the present invention is read out quantatively the concentration of atomic elements in a specimen tissue, which can be samples of blood, urine feces, saliva, skin, bone, or any other tissue. Calcium, for example, regulates the excitability of nerve and muscle, its concentration controls electric resistance across the axon membrane and the liberation of acetylcholine. Is is needed for the genesis of fibrin. Intracellular calcium is essential for contraction, is needed by enzymatic systems in mitochondria and the organelles. Hyper-(or hypo) calcemia is shown in many diseases such as hyer-(or hypo) thyroidism and parathyrodism, sarcoidosis, metastatic osteolytic, certain infant morbid phenomenon, the milk-alkali syndrome, abnormal adrenal steriods, rickets, osteoporosis, ostenoblastic metastasis, Cushing's syndrome, etc., etc. Atomic absorption spectroscopy is currently the most accurate test. With a K-absorption edge for Ca at 4.0381 KeV and with a standard specimen as calibration, it is simply to read out the mole-fraction of it directly from the tissue without destroying it. The sensitivity of this method can very well be better than that of the spectroscopic test. Consideration iron as the next designated element. It is well known for hemoglobin metabolism, and is also vital in several intracellular functions. Iron deficiency shows up most commonly in anemia. Gastrointestinal bleeding, renal disease, chronic infection or severe inflammatory diseases, scurvy, etc. give rise to or caused by hpyoferremia, while liver diseases, sideroachrestic anemias, aplastic anemias, Kaschin-Beck disease, hemolytic and hemorrhagic disorders, etc. give rise to or caused by hyperferremia. With K-edge at 7.1112 KeV, the quantitative measurement of Fe in serum can be performed simply.

Several other metals which are important co-factors in many vital enzymes can also be measured similarly. They are, copper(K-edge at 8.9803 KeV; Wilson's disease, Kwashiorkor, malabsorption syndrome, nephrotic syndrome, multiple sclerosis, psoriasis, certain liver diseases, atherosclerosis, etc.), zinc (K-edge at 9.6607 KeV; Hodgkin's disease, leukemia, chronic alcolholism, hepatitis, pernicious anemia, etc.), manganese (K-edge at 6.5376 KeV; anorexia, asthenia, certain psychotic behavior, etc. from chronic inhalation of the element, and derangements in lipid metabolism, etc. from deficiency of it).

The fact that the elements can be measured without performing any chemical assay, one tissue sample can be analyzed for all the elements in question. Using Bragg spectrometer for a tunable beam of monochromatic X-ray, each element merely corresponds to a different angle of the Bragg diffraction, and a single pair of Bragg crystals can probably cover an energy range from 4 to 10 KeV, that is, covering all the elements mentioned above. Limit the amount of tissue required for various tests is an important merit.

EXAMPLE 2

Indirect Assay for Immunological Measurements

The occurance of tyrosyl residues in almost all proteins is the basis for choosing iodine as "label" for proteins. In is the same way as occurs naturally in thyroid hormones, and the ring structure of tyrosine may incorporate one or two iodine, which must first be oxidized prior to the linkage of the ring structure.

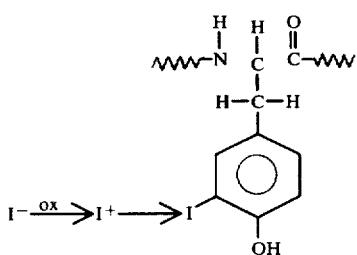

This method of iodination is convenient and is therefore generally chosen. With this invention this method may be used to tag immunoproteins such as antibodies or complements. Iodine is a very heavy atom, and its introduction may change the overall shape of the protein as well as the pK value of tyrosyl residue and its immediate vicinity. Iodinated tyrosine should therefore locate as far away from the active binding site as possible in order not to interfere with immunobinding reactions. There are several standard methods such as precoupling to a solid phase matrix to hide the site, using hapten as carrier, etc. to resolve the problem of chemical interference from iodination.

A great variety of hormones, steroids, can be injected, as antigens, into animals in order to produce "pure" antibodies, and they are harvested, processed, and sold "off-the-shelf" for clinical applications. Sometimes even certain vitamin, immunoglobulin, certain tumor related products such as carcinoembronic antigen, α-fetoprotein, or even certain drugs such as digoxin, all can be injected as antigens and have their particular antibodies from the animals harvested processed.

All immunoassays with the use of radioactive iodine can most likely be improved by the use of cold iodine with our method. I can employ "standard specimens" as calibrations to compare the specimen in question and immediately obtain the quantitative information. If the immunoprecipitate and the iodinated antibodies can be separated from the specimen very cleverly without destroying the specimen, the same specimen can perhaps be measured against a variety of antibodies. To limit the specimen requirement from a clinical environment is an ever present challenge, and this invitro method, non-intrusive to the sample, may help in this direction.

EXAMPLE 3

Analog Compound with Heavy Elements to Identify Metabolic Pathways

BrdU functions exactly like thymidine except a slight change of pH value, and in a DNA double helix, the Br atom points away from the base pairs. BrdU has a variety of other properties that can serve useful purpose. Br is covalently bound to the base U and is therefore extremely stable. Being part of DNA in a cell, BrdU can be replaced by thymidine as a cellular repair, and the uptake of the compound can greatly be enhanced by antimetabolic agents such 5-FU, methotrexate, etc. Using a precursor form BrdC, the enzyme, deoxycytidylate deaminase transforms it to BrdU, but it can be blocked by tetrahydrouridine in many mammalian systems, while in herpes viruses infected systems, there is an additional pathway of deaminase and the transformation to BrdU cannot be blocked by $H_4u$. With this information in mind, one can feed the herpes DNA with BrdU or BrdC, and trace its development or movement with the bromine detector of our method.

BrdU serves simply as a source of Auger electrons to be induced by a monochromatic X-ray beam for the K-edge of bromine. This arrangement can perform anything that $^3$H-thymidine can function, with the added advantage that no waiting for the decay of tritium, of course.

EXAMPLE 4

Miscellaneous Examples of Application

A dye bromsulfophthalein is often used in vivo in the blood system and can usually very quickly be extracted by the liver cells. The dye changes the color of the blood, and its disappearance from the blood is an indication of the detoxication function of the liver. With out method of identifying the bromine element in the serum, only trace amount of the blood would be required, it can probably be examined non-instrusively, and therefore the liver function be monitored continuously, perhaps as a probe for some other drugs.

EXAMPLE 5

Measurement of Serum Thyroxine

L-thyroxine, or commonly called

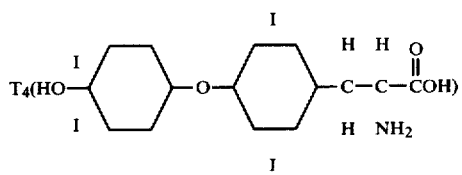

is made of two molecules of diiodotyrosine, and is one of the two principle thyroid hormones. The other one is l-triiodothyronine ($T_3$) which is identical to $T_4$ except with one less iodine under the circle I. In serum, $T_4$ molecules are mostly transported with plasma proteins such as $T_4$-binding globulin, $T_4$-binding prealbumin, and albumin. A very small fraction of $T_4$ in serum is in free form, usually 0.04–0.05%, and it is the active moiety which enters cells and stimulates metabolism. The protein bound $T_4$ acts as a reservoir of the free $T_4$ and at the same time buffers peripheral tissues against the total metabolic effects of the hormone in the blood.

in order to measure the serum level of total $T_4$ in our X-ray immunoassay, the following four steps are necessary:

(1) separate $T_4$ from its carrier protein, (2) attach $T_4$ to $T_4$-specific antibody or $T_4$-specific protein such as the $T_4$-binding globulin in order to form a $T_4$-complex, (3) separate the $T_4$-complex from the rest of the specimen, and finally, (4) use X-ray technique to measure iodine atoms as an indication of $T_4$. For step (1), the extraction of $T_4$ from its carrier protein can be heat, strong acid, ethanol, or use chemicals such as 8-anilino-1-naphthalene sulfonic acid or sodium salicylate to effectively compete for the proteein binding sites. $T_4$ is a small molecule with high density. It has a molecular weight of 769, contributed mostly from the four iodine atoms. A gel filtration would free $T_4$, together with other small molecules, from the sample. A centrification would further concentrate $T_4$.

For step (2), anti-$T_4$-antiserum as harvested from animals, or simply the $T_4$-binding globulin picks up very specifically only $T_4$ from step (1) to form a $T_4$-complex. If this specific antibody or globulin can be bound to a solid phase, such as a polytetrafluoroethylene disc, it will greatly simplify both steps (1) and (3). One needs only to dip the antibody-coated disc to a $T_4$ sample where the carrier protein has been separated, wash away all but $T_4$-comples, and measure the additional iodine contributed from $T_4$.

For step (3), $T_4$-complex can be separated again by gel filtration, except here only the large molecules are retained, and they form the specimen for X-ray measurements, which is step (4). Prior to the formation of the $T_4$-complex, the level of iodine presence in the antibody and in the solid phase disc must be measuured with our non-intrusive X-ray technique in order to form a base level of calibration. With the $T_4$-complex, we read the additional iodine contribution which is proportional to $T_4$.

From steps (1) to (3), the methods were taken from "standard" competive protein binding or from "standard" radioimmunoassay. Over the years, there were many developments on the assaying of $T_4$, particularly in radioimmunoassay where the use of a solid phase antibody to fish out the desired $T_4$ antigen is indeed very convenient. We shall follow these procedures when possible, and expect to derive at the same sensitivity from each of the steps. In fact, we shall use the same RIA Kits for the chemical materials involved in the steps. But being able to measure the atomic concentration directly, we cut short the assaying process with our step (4). We no longer need to add labeled antigens for competitive binding, no longer need to incubate extensively for all of the immunoreactants, no longer require to use a minimal limit for statistical accuracy that is inherent to the radioactivity problem, and most important of all, we no longer need to wait for labeled isotopes to decay. With a much shortened chemical procedure, we may anticipate a greatly improved overall sensitivity and efficiency.

In many other RIA or enzyme immunoassay, $T_4$ is often employed as a hapten to be bound covalently to a macromolecule M. If the anti-$T_4$M (or tyrosine-M) antibody can be harvested from the animals, and if there is little or no iodine in Molecule M, we can perhaps follow similarly the above mentioned procedures to assay a variety of these molecules M. Note that immunoreaction is very complex and it is affected by the pH, temperature, ionic strength of the solution, time, and the ratio of antibody to antigen. With our non-intrusive reading of the specimen, several data points may be obtained as considered in step (4) while the immunoreaction is still in progress. These data points can be checked against a standard reference and thereby provide us far more handles on the assay. On the market, there are many RIA Kits designed for a variety of tests that use labeled iodine for the labeled antigen. These tests are good candidates for the molecule M.

I claim:

1. A method of detecting, in a specimen, atoms, of a particular element having an atomic number of at least 20, comprising irradiating the specimen with monochromatic X-rays having a wavelength to induce an inner shell ionization of said atoms with subsequent auger cascade, and detecting the auger electrons emitted by the cascade wherein the specimen is irradiated alternately with X-rays of said wavelength and with X-rays of a wavelength less than said wavelength and the difference between the auger electrons detected at said wavelength and at the shorter wavelength is determined.

2. A method according to claim 1, wherein the quantity and distribution of the atoms is recorded on a photographic emulsion which itself includes substantially no atoms of the element.

3. A method according to claim 2, wherein the photographic emulsion is a layer disposed closely adjacent the specimen.

4. A method according to claim 3, wherein the specimen is a biological specimen in the form of a specimen slide and the photographic emulsion is a liquid emulsion coated directly on the specimen slide.

5. A method according to claim 1, including producing the monochromatic X-rays by exposing a secondary radiator having atoms of an element which when exposed to X-rays produces excitation of these atoms and consequent secondary radiation in the form of X-rays of said wavelength.

6. A method according to claim 1 wherein the inner shell ionization is converted to usable light by tellurium disposed adjacent the specimen.

7. A method according to claim 6, wherein a matrix of x-ray opaque material is disposed between the source of monochromatic x-rays and the specimen and the tellurium is distributed in a matrix in optical alignment with the first mentioned matrix, whereby the tellurium is shielded from exposure to the monochromatic x-rays from the source.

8. A method according to claim 1, wherein the secondary radiator has at least two discrete radiating areas, at least one said area including atoms of said area including atoms of an element which when exposed to said secondary radiation producing element and at least another said X-rays produces excitation of these atoms and consequent secondary radiation in the form of X-rays of a wavelength less than that required to induce an inner shell ionization of the atoms to be detected in the specimen and selectively exposing the specimen to secondary radiation from a said one or a said another of the areas.

9. A method according to clam 8, wherein the secondary radiator is a disc arranged for rotation about its axis and the areas are spaced circumferentially about the axis so that upon rotation of the disc the areas are exposed alternately to X-rays thereby alternately to expose the specimen to secondary radiation from the one and another areas.

10. A method according to claim 8, wherein the specimen is alternately and repeatedly exposed to secondary radiation from said one and said another of the areas.

11. A method according to claim 8, wherein the difference between the detected auger electrons emitted by the cascade when the specimen is exposed to secondary radiation from a said one area and from a said another area is determined to provide an output representing an accurate quantitive indication of the auger electrons emitted by the atoms to be detected.

12. A method according to claim 11, wherein the auger electrons are detected as to quantity and distribution and the difference is determined as to quantity and distribution.

13. A method according to claim 1, wherein the monochromatic X-rays are emitted by a Bragg diffractor.

14. A method according to claim 1, wherein a Bragg diffractor is cyclically adjusted to emit X-rays at said wavelength alternately with X-rays at a wavelength less than that required to induce an inner shell ionization of the atoms to be detected in the specimen and exposing the specimen to said cyclically adjusted X-rays.

15. A method according to claim 1, wherein the specimen is biological and the element to be detected is iodine or bromine.

16. A method according to claim 1 wherein the quantity and distribution of the atoms is recorded by an electrostatic image produced by the auger electrons emitted.

17. A method according to claim 16 wherein the electrostatic image is produced and recorded by the establishment of an electrostatic image produced by the auger electrons and the production of a permanent image therefrom.

18. A method according to claim 16 wherein the image is produced and recorded by xerography.

19. A method according to claim 1 wherein the quantity and distribution of the atoms is recorded by a charge coupled device.

20. A method according to claim 19 wherein the specimen is alternately exposed to different magnitudes of x-ray energy, the auger electron emission resulting from each of which is recorded by the charge coupled device and stored in a memory, the difference in the recorded information providing a spacial and quantitative indication of the particular element to be detected.

21. Apparatus according to claim 1 wherein the detecting means comprises a charge coupled device.

22. Apparatus according to claim 21 comprising means for alternately exposing the specimen to different magnitudes of X-ray energy, memory means for storing the detected auger electron emissions resulting from the different magnitudes of x-ray energy and a differential amplifier for ascertaining the difference between the stored information and providing a spacial and quantitative indication of the particular element to be detected.

23. Apparatus for detecting, in a specimen, atoms, of a particular element having an atomic number of at least 20, comprising a source of monochromatic X-rays having a wavelength to induce an inner shell ionization of said atoms with subsequent auger cascade, and means for detecting the auger electrons emitted by the cascade, wherein the source is adapted to irradiate the specimen alternately with X-rays of said wavelength and with X-rays of a wavelength less than said wavelength and means are adapted to determine the difference between auger electrons detected at said wavelength and at the shorter wavelength.

24. Apparatus according to claim 23, wherein the detecting means is a photographic emulsion which includes substantially no atoms of the element.

25. Apparatus according to claim 24, wherein the specimen is a biological specimen slide and the emulsion is a liquid emulsion coated onto the slide.

26. An Apparatus according to claim 23 wherein the inner shell ionization is converted to usable light by a tellurium disposed adjacent the specimen.

27. Apparatus according to claim 26 wherein a matrix of x-ray opaque material is disposed between the source of monochromatic x-rays and the specimen and the tellurium is distributed in a matrix in optical alignment with the first mentioned matrix, whereby the tellurium is shielded from exposure to the monochromatic x-rays from the source.

28. Apparatus according to claim 23, wherein the source includes a secondary radiator having atoms of an element which upon irradiation by X-rays will produce excitation of the atoms and consequent secondary radiation in the form of X-rays of said wavelength.

29. Apparatus according to claim 28, wherein the radiator is a flat plate.

30. Apparatus according to claim 28 wherein the secondary radiator has at least two discrete radiating areas, at least one said area including atoms of said secondary radiation producing element and at least another said area including atoms of an element which when exposed to said X-rays produces excitation of these atoms and consequent secondary radiation in the form of X-rays of a wavelength less than that required to induce an inner shell ionization of the atoms to be detected in the specimen and means for selectively exposing the specimen to secondary radiation from a said one or a said another of the areas.

31. Apparatus according to claim 30, wherein means alternately and repeatedly expose the specimen to secondary radiation from a said one and a said another of the areas.

32. Apparatus according to claim 30, wherein the secondary radiator is a disc arranged for rotation about its axis and the areas are spaced circumferentially about the axis so that upon rotation of the disc the areas are exposed alternately to X-rays thereby alternately to expose the specimen to secondary radiation from a said one and a said another of said areas.

33. Apparatus according to claim 32, including means for rotating the disc and means associated therewith for providing an output signal representative of the rate and rotational position of the disc, and means for determining the difference between auger electrons detected at said wavelength and at said shorter wavelength on the basis of information received by said difference means from said detecting means and said output signal.

34. Apparatus according to claim 28, wherein the source includes an X-ray generator.

35. Apparatus according to claim 23, wherein the difference means is a lock-in amplifier.

36. Apparatus according to claim 23, wherein a Bragg diffractor is arranged to emit the monochromatic X-rays.

37. Apparatus according to claim 23, wherein the source includes a Bragg diffractor which is cyclically adjustable to emit X-rays at said wavelength alternately with X-rays at a wavelength less than that required to induce an inner shell ionization of the atoms to be detected in the specimen and exposing the specimen to said cyclically adjusted X-rays.

38. Apparatus according to claim 23, including means for relatively positioning the source, specimen and detecting means for the irradiation of the specimen by the monochromatic X-rays and the detection of the resulting auger cascade.

39. Apparatus according to claim 23 comprising means for recording the distribution of the atoms by the production of an electrostatic image produced by the auger electrons emitted.

40. Apparatus according to claim 39 comprising means for producing an electrostatic image produced by the auger electrons and means for producing a permanent image therefrom.

41. Apparatus according to claim 40 comprising xerographic means for producing and recording the electrostatic image.

* * * * *